(12) United States Patent
Yaroslavsky et al.

(10) Patent No.: US 7,627,363 B2
(45) Date of Patent: Dec. 1, 2009

(54) POLARIZED LIGHT IMAGING DEVICES AND METHODS

(75) Inventors: Anna N. Yaroslavsky, Boston, MA (US); R. Rox Anderson, Boston, MA (US)

(73) Assignee: The General Hospital Corporation, Boston, MA (US)

(*) Notice: Subject to any disclaimer, the term of this patent is extended or adjusted under 35 U.S.C. 154(b) by 383 days.

(21) Appl. No.: 10/803,329

(22) Filed: Mar. 18, 2004

(65) Prior Publication Data

US 2004/0249274 A1 Dec. 9, 2004

Related U.S. Application Data

(60) Provisional application No. 60/455,614, filed on Mar. 18, 2003.

(51) Int. Cl.
*A61B 5/05* (2006.01)
*A61B 6/00* (2006.01)

(52) U.S. Cl. .............. 600/473; 600/474; 600/475; 600/476; 600/477; 600/407

(58) Field of Classification Search ........... 600/407, 600/473–477
See application file for complete search history.

(56) References Cited

U.S. PATENT DOCUMENTS

| | | |
|---|---|---|
| 4,541,438 A | 9/1985 | Parker et al. |
| 4,768,513 A | 9/1988 | Suzuki |
| 5,042,494 A | 8/1991 | Alfano |
| 5,079,262 A | 1/1992 | Kennedy et al. |
| 5,115,137 A | 5/1992 | Andersson-Engels et al. |
| 5,131,398 A | 7/1992 | Alfano et al. |
| 5,205,291 A | 4/1993 | Potter |
| 5,261,410 A | 11/1993 | Alfano et al. |
| 5,270,788 A | 12/1993 | Cercek et al. |
| 5,363,854 A | 11/1994 | Martens et al. |

(Continued)

FOREIGN PATENT DOCUMENTS

GB 2254417 A 10/1992

(Continued)

OTHER PUBLICATIONS

Brancaleon L, Durkin AJ, Tu JH, Menaker G, Fallon JD, Kollias N: In vivo fluorescence spectroscopy of nonmelanoma skin cancer. *Photochem.Photobiol.* 73(2): 178-183, 2001.

(Continued)

*Primary Examiner*—Brian Casler
*Assistant Examiner*—James Kish
(74) *Attorney, Agent, or Firm*—Edwards Angell Palmer & Dodge LLP; Peter C. Lauro, Esq.; George N. Chaclas, Esq.

(57) ABSTRACT

The present invention is directed to a novel multi-spectral contrast agent-enhanced polarized light imaging technique that enables rapid imaging of large tissue fields. The imaging device includes a tunable monochromatic light source and a CCD camera. Linear polarizers are placed into both the incident and collected light pathways in order to limit the measurement volume to the superficial tissue layers. To enhance the tumor contrast in the image, aqueous solutions of toluidine blue or methylene blue are topically applied.

16 Claims, 10 Drawing Sheets

U.S. PATENT DOCUMENTS

| | | | |
|---|---|---|---|
| 5,413,108 | A | 5/1995 | Alfano |
| 5,579,773 | A | 12/1996 | Vo-Dinh et al. |
| 5,634,922 | A | 6/1997 | Hirano et al. |
| 5,647,368 | A | 7/1997 | Zeng et al. |
| 5,836,999 | A * | 11/1998 | Eckhouse et al. ............. 607/88 |
| 5,847,394 | A * | 12/1998 | Alfano et al. ............ 250/341.8 |
| 5,929,443 | A * | 7/1999 | Alfano et al. ............ 250/341.3 |
| 5,971,767 | A * | 10/1999 | Kaufman et al. ............ 434/267 |
| 5,983,120 | A * | 11/1999 | Groner et al. ............... 600/310 |
| 6,032,071 | A | 2/2000 | Binder |
| 6,070,093 | A | 5/2000 | Oosta et al. |
| 6,083,487 | A | 7/2000 | Biel |
| 6,091,983 | A * | 7/2000 | Alfano et al. ............... 600/431 |
| 6,091,985 | A | 7/2000 | Alfano et al. |
| 6,123,719 | A | 9/2000 | Masychev |
| 6,135,965 | A | 10/2000 | Tumer et al. |
| 6,175,759 | B1 | 1/2001 | Chan et al. |
| 6,208,886 | B1 * | 3/2001 | Alfano et al. ............... 600/473 |
| 6,256,530 | B1 | 7/2001 | Wolfe |
| 6,258,576 | B1 | 7/2001 | Richards-Kortum et al. |
| 6,317,624 | B1 | 11/2001 | Kollias et al. |
| 6,352,502 | B1 | 3/2002 | Chaiken et al. |
| 6,587,711 | B1 | 7/2003 | Alfano et al. |
| 6,593,101 | B2 * | 7/2003 | Richards-Kortum et al. .. 435/29 |
| 6,615,061 | B1 * | 9/2003 | Khalil et al. ................ 600/310 |
| 6,665,557 | B1 * | 12/2003 | Alfano et al. ............... 600/473 |
| 6,674,527 | B2 | 1/2004 | Hoyt |
| 6,766,184 | B2 * | 7/2004 | Utzinger et al. ............. 600/407 |
| 2002/0065468 | A1 | 5/2002 | Utzinger et al. |
| 2003/0026762 | A1 | 2/2003 | Malmros et al. |
| 2003/0236458 | A1 * | 12/2003 | Hochman ................... 600/431 |
| 2004/0006275 | A1 * | 1/2004 | Demos et al. ................ 600/476 |
| 2004/0249274 | A1 * | 12/2004 | Yaroslavsky et al. ........ 600/431 |
| 2006/0132790 | A1 | 6/2006 | Gutin |

FOREIGN PATENT DOCUMENTS

| | | |
|---|---|---|
| JP | 53122489 A | 10/1978 |
| WO | WO-93/13403 A1 | 7/1993 |
| WO | WO-97/06724 A1 | 2/1997 |
| WO | WO-01/39665 A2 | 6/2001 |
| WO | 2006076810 A1 | 7/2006 |

OTHER PUBLICATIONS

Hewett J, Nadeau V, Ferguson J, Moseley H, Ibbotson S, Allen JW, Sibbett W, Padgett M: The application of a compact multispectral imaging system with integrated excitation source to in vivo monitoring of fluorescence during topical photodynamic therapy of superficial skin cancers. *Photochem.Photobiol.* 73(3): 278-282, 2001.

Bugaj JE, Achilefu S. Dorshow RB, Rajagopalan R. Novel fluorescent contrast agents for optical imaging of in vivo tumors based on a receptor-targeted contrast agent-peptide conjugate platform. *JBiomed Opt* 6:122-33, 2001.

Jacques SL, Roman JR, Lee K: Imaging superficial tissues with polarized light. *Las.Surg.Med.* 2000; 26:119-129.

Andersson-Engels S, Canti G, Cueddu R, Eker C, of Klinteberg C, Pifferi A, Svanberg K, Svanberg S, Taroni P, Valentini G, Wang I: Preliminary evaluation of two fluorescence imaging methods for the detection and the delineation of basal cell carcinomas of the skin. *Las. Surg Med.* 26:76-82, 2000.

West JL and Halas NJ: Applications of Nanotechnology to Biotechnology—Commentary. *Current Opinion in Biotechnology* 11: 215-220, 2000.

Douven LFA, Lucassen GW: Retrieval of optical properties of skin from measurement and modeling the diffuse reflectance. *Proc SPIE* 3914: 312-323, 2000.

Wennberg AM, Gudmundson F, Stenquist B, Ternesten A, Moelne L, Rosen A, Larko O: In vivo detection of basal cell carcinoma using imaging spectroscopy. *Acta Derm. Venereol.* 79: 54-61, 1999.

Kaisary AV: Assessment of radiotherapy in invasive bladder carcinoma using in vivo methylene blue staining technique. *Urology*, 28(2): 100-102, 1986; Eisen GM, Montgomery EA, Azumi N, Hatmann D-P, Bhargava P, Lippman M, Benjamin SB: Qualitative mapping of Barrett's metaplasia: a prerequisite for intervention trials. *Gastrointestinal Endoscopy*, 50 (6): 814-818, 1999.).

Svaasand LO, Norvang LT, Fiskerstrand EJ, Stopps EKS, Berns MW, Nelson JS: Tissue parameters determining visual appearance of normal skin and port-wine stains. *Las Med Sciences* 10: 55-65, 1995.

Oseroff AR, Ohuoha D, Ara G, McAuliffe D, Foley J, Cincotta L: Intramitochondrial contrast agents allow selective in vitro photolysis of carcinoma cells. *Proc. Natl. Acad. Sci.*USA, 83: 9729-9733, 1986.

Supplementary European Search Report dated Mar. 9, 2007.

* cited by examiner

Methylene Blue (MB⁺) : $R_1=R_2=R_3=R_4=CH_3$  $R_5=H$

Toluidine Blue (TB⁺) :  $R_1=R_2=R_5=CH_3$  $R_3=R_4=H$

POLARIZED LIGHT IMAGING DEVICES AND METHODS

CROSS-REFERENCE TO RELATED APPLICATIONS

This application claims the benefit of U.S. Provisional Application No. 60/455,614 filed Mar. 18, 2003, the entire contents of which are incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

FIELD OF THE INVENTION

The present invention is directed to a real-time method for imaging organic tissue. The method employs a polarization-enhanced reflectance/imaging system in order to obtain images of the organic tissue. The obtained images can be used in the demarcation of, among other things, nonmelanoma skin cancers.

BACKGROUND OF THE INVENTION

Nonmelanoma skin cancers are the most common forms of human cancer. About 75% of all skin cancers are basal cell carcinomas (BCC) and about 20% are squamous cell carcinomas (SCC). These cancers are a major cause of morbidity in the Caucasian population. They commonly appear on sun-exposed areas of the body such as the head and neck. Since many tumors occur on the face it is imperative to preserve normal skin surrounding the tumor. Unfortunately, most of these tumors have poorly defined boundaries, which makes visual detection of the tumor borders and, consequently, precise excision a challenging problem. In the US, Mohs micrographic surgery (MMS) is an accepted procedure that removes as little normal skin as possible while providing the highest cure rate. Using detailed mapping and complete microscopic control of the excised lesion the Mohs surgeon can pinpoint areas at the surgical margins involved with cancer that are otherwise invisible to the naked eye. While precise and accurate, MMS is also a time-consuming and staff-intensive procedure. It requires a surgeon trained in dermatopathology, a dedicated laboratory and a technician to prepare and evaluate frozen sections. Because of these shortcomings, MMS is used in the minority of cases.

In recent years, the development of optical imaging modalities led to the introduction of techniques that may become a viable alternative to the existing methods of skin tumor detection and demarcation. However, all these techniques lack one or more elements necessary for their practical use in a clinical setting.

Confocal reflectance microscopy has been used to study different normal and pathological skin conditions. It allows imaging within turbid media with high resolution (lateral ~1 μm, axial (section thickness) ~3 μm), which is comparable to histology. The major disadvantage of in vivo confocal microscopy for the assessment of skin tumor margins is the small field of view (0.25 mm to 0.3 mm). By sacrificing axial resolution (~30 μm) it is possible to enlarge the field of view up to 2 mm. But even 2-mm field of view is much smaller than the size of most lesions. To examine the entire suspected cancerous area the sequences of images should be captured and stitched together. This process takes time and the resulting image may be distorted by patient's motion.

Polarized light has been used extensively for biological and medical applications. In most cases, skin cancer arises from epidermis. As such, for detection of skin lesions, it is advantageous to acquire superficial images. To achieve this goal while retaining a large field of view polarized light imaging may be employed. The use of polarized light allows imaging of the superficial tissue layers only. When the light incident on the sample is linearly polarized, the two images acquired with the co-polarized and cross-polarized light can be used to largely isolate the single-scattered component, which arises mainly from superficial skin layers. If a turbid medium, like skin, is illuminated with a linearly polarized light, the back-scattered light partially retains its polarization. The light that is specularly reflected and single-scattered by a random turbid medium has the same polarization as the incident beam. For example, let $IM_p^s$ be the intensity of single scattered light at the image plane. Multiple scattering randomizes polarization of the propagating beam. Eventually, half of the multiple backscattered light has the same polarization ($IM_p^m$), and another half has a polarization transversal ($IM_s^m$) to the incident beam polarization, consequently $IM_p^m = IM_s^m$.

Conventional image, IM, is created by single scattered light and multiple scattered light:

$$IM = IM_p^s + IM_p^m + IM_s^m. \quad (1)$$

An image acquired using the remitted light polarized in the direction parallel to the polarization of the incident light is created by a sum of single scattered light and multiple scattered light:

$$IM_p = IM_p^s + IM_p^m. \quad (2)$$

An image acquired using the remitted light polarized in the direction transversal to the polarization of the incident light is created by multiple scattered light only:

$$IM_s = IM_s^m. \quad (3)$$

The difference image, DIM, is obtained by subtraction:

$$DIM = IM_p - IM_s = IM_p^s + IM_p^m - IM_s^m = IM_p^s. \quad (4)$$

This image is formed by single scattered light since, as it was explained above, $IM_p^m = IM_s^m$.

Single backscattering happens in skin, depending on the wavelength of light, pigmentation, and blood content, at the depth of approximately 70 μm to 200 μm in the visible and near infrared spectral range. Recently, white polarized light digital imaging was being used to evaluate pigmented skin lesions. (Jacques S L, Roman J R, Lee K: Imaging superficial tissues with polarized light. *Las. Surg. Med.* 2000; 26:119-129.) A polarization image, PIM, was created and analyzed:

$$PIM = \frac{IM_p - IM_s}{IM_p + IM_s} \quad (5)$$

The numerator is equal to DIM. The denominator is a conventional image. The ratio of the difference image to the conventional image can be used to cancel out the contrast that is associated with any superficial chromophore (i.e. melanin, blood) present in the tissue. The thickness of the imaged layer is about 200 μm (white light). Melanin strongly scatters light, producing bright areas with excellent contrast in pigmented lesions. Such high contrast based on scattering would not be expected to occur reliably in nonmelanoma skin cancers, which contain variable amounts of melanin. Thus, this method includes an inability to use spectral information encoded in white light image for lesion characterization and comparatively poor contrast of the nonmelanoma cancer lesion in the image.

Considerable efforts have been devoted to the development of skin tumor imaging techniques based on detection of endogenous fluorescence and exogenous fluorescence of photosensitizers. In Brancaleon et al. the possibility of using autofluorescence (endogenous fluorescence) spectroscopy for the detection of nonmelanoma skin cancer was explored. (Brancaleon L, Durkin A J, Tu J H, Menaker G, Fallon J D, Kollias N: In vivo fluorescence spectroscopy of nonmelanoma skin cancer. Photochem. Photobiol. 73(2): 178-183, 2001.) Their in vivo and in vitro studies have shown that the endogenous fluorescence of tryptophan residues was stronger and fluorescence associated with collagen and elastin was weaker in tumor than in normal tissue. At the same time the authors mentioned that in the case of morpheaform BCC, when collagen fibers are surrounded with tumor cells, and SCC in situ, when there is no tumor invasion into the dermis, the collagen fluorescence might increase. The loss of collagen and elastin fluorescence in the vicinity of a tumor was observed for 78% of fresh frozen cancer tissue samples. The areas characterized by the loss of fluorescence were two- to threefold larger than the tumor size determined from histological evaluation. Therefore, the method suggested in the paper may be applied for nonmelanoma cancer detection, but cannot be used for precise tumor demarcation during surgery.

Photodynamic therapy (PDT) has also been tried as an alternative method for treatment of skin cancers. An example of a PDT procedure for dermatology involves the topical application of δ-aminolevulinic acid (ALA) followed by irradiation with red light (λ~635 nm). ALA is a precursor in the biosynthesis of protoporphyrin IX (Pp IX) that accumulates in tumor tissue. When cells containing Pp IX are irradiated with red light, they are selectively killed. Pp IX is fluorescent, and therefore, may be used for tumor detection. Wennberg et al imaged in vivo the areas of Pp IX fluorescence and compared the location and the size of these areas with the size of the lesions determined by histological methods. (Wennberg A M, Gudmundson F, Stenquist B, Ternesten A, Moelne L, Rosen A, Larko O: In vivo detection of basal cell carcinoma using imaging spectroscopy. Acta Derm. Venereol. 79: 54-61, 1999.) They found that in 50% of lesions the correlation with histology was good, in 23% the correlation was partial, and in 27% there was no correlation at all. The authors noticed that the selectivity of Pp IX fluorescence is not high enough, since in several cases Pp IX fluorescence was detected from sun-damaged skin, healing scars, and normal hair follicles. Similar studies, which employed multi-wavelength fluorescence and lifetime fluorescence imaging, were conducted by several other groups. The predictive capability of Pp IX fluorescence imaging and its ability to demarcate lateral extent of the tumor are still questionable. (Hewett J, Nadeau V, Ferguson J, Moseley H, Ibbotson S, Allen J W, Sibbett W, Padgett M: The application of a compact multispectral imaging system with integrated excitation source to in vivo monitoring of fluorescence during topical photodynamic therapy of superficial skin cancers. Photochem. Photobiol. 73(3): 278-282, 2001; Andersson-Engels S, Canti G, Cueddu R, Eker C, af Klinteberg C, Pifferi A, Svanberg K, Svanberg S, Taroni P, Valentini G, Wang I: Preliminary evaluation of two fluorescence imaging methods for the detection and the delineation of basal cell carcinomas of the skin. Las. Surg. Med. 26:76-82, 2000.)

In many cases the differences of optical signals from normal and diseased tissues are subtle, therefore a lot of effort is devoted to the development and evaluation of novel optical contrast agents. Gold nanoparticles and microspheres filled with light scattering media are examples of such contrast agents. (West J L and Halas N J: Applications of Nanotechnology to Biotechnology—Commentary. Current Opinion in Biotechnology 11: 215-220, 2000.) The advantage of these contrast agents is the tunability of their optical properties. In other words, using the structure, the size, and the refractive index as variable parameters it is possible to create the particles, which will enhance scattering and/or absorption of the tissue containing these particles at the specific predefined wavelengths. The utility of such contrast agents greatly depends on the efficiency of their delivery to the target tumor tissue. One of the approaches is to design very selective contrast agents that could be injected intravenously and that would migrate and localize into a tumor. Another one is to bind the existing contrast agents to specific cell surface proteins thus achieving tumor selectivity. (Bugaj J E, Achilefu S, Dorshow R B, Rajagopalan R. Novel fluorescent contrast agents for optical imaging of in vivo tumors based on a receptor-targeted contrast agent-peptide conjugate platform. J Biomed Opt 6:122-33, 2001.) The development of these state of the art molecular specific contrast agents is a complex and challenging problem. Elaborate and time-consuming animal model testing is required to evaluate the potential of these approaches for in vivo tumor imaging in humans. At this point of development it is not feasible to attempt application of these experimental contrast agents in clinical practice. Where BCC is concerned, investigation of applicability of such molecular-specific agents is even more problematic, since there exists no animal model for BCC of human skin. Therefore an approach based on utilization of the existing contrast agents appears to be more suitable for applications in present clinical settings.

The nontoxic contrast agents that are selectively retained by cancerous tissue have been applied previously to aid in visual examination of oral, bladder, and cervix lesions. Phenothiazinium contrast agents including methylene blue (MB) and toluidine blue (TB) in particular have been used for staining various carcinomas in vivo. (Kaisary A V: Assessment of radiotherapy in invasive bladder carcinoma using in vivo methylene blue staining technique. Urology, 28(2): 100-102, 1986; Eisen G M, Montgomery E A, Azumi N, Hatmann D-P, Bhargava P, Lippman M, Benjamin S B: Qualitative mapping of Barrett's metaplasia: a prerequisite for intervention trials. Gastrointestinal Endoscopy, 50 (6): 814-818, 1999.) Phenothiazinium contrast agents are accumulated to a much greater extent in mitochondria of carcinoma cells compared to normal cells. (Oseroff A R, Ohuoha D, Ara G, McAuliffe D, Foley J, Cincotta L: Intramitochondrial contrast agents allow selective in vitro photolysis of carcinoma cells. Proc. Natl. Acad. Sci. USA, 83: 9729-9733, 1986.) MB has been successfully applied to grossly demarcate neoplastic tumors in bladder, tumors of pancreas, and Barrett's esophagus metaplasia. TB has been used topically to detect oral carcinoma, and Barrett's esophagus metaplasia.

TB is a preferred stain for use in Mohs surgery for BCC, because TB staining provides some advantages relative to hematoxylin-eosin (H&E) including a highly identifiable staining pattern (metachromasia) of BCC. Since TB is routinely used to stain fresh-frozen tissue sections during MMS, the processed polarized light images of stained tumors are remarkably similar to standard Mohs micrographic surgery maps. This similarity significantly simplifies the process of image understanding and interpretation for a Mohs surgeon. Hair follicles, sebaceous glands, fat, and normal stromal elements are visible in detail, and appear differently from the tumor, which appears very dark due to the increased, relative to the normal tissue, uptake of the contrast agent.

Another type of contrast agents used is fluorescent contrast agents (fluorophores). Fluorescent contrast agents absorb light at the specific wavelengths and emit light at longer wavelengths. There are several fluorophores that preferentially stain tumors and, therefore, can be used for tumor detection and demarcation. These include: Pp IX, tetracycline, TB, and MB. Fluorescence spectra are sensitive to the changes in biochemical environment of the fluorophore molecules. Biochemical composition of the diseased skin differs significantly from the normal. Therefore fluorescence imaging gives a promise of further increasing the specificity of the contrast agents like TB, MB, and TCN.

SUMMARY OF THE INVENTION

All of the above mentioned approaches attempted so far for bedside imaging of skin cancer, have advantages and drawbacks. It appears, however, that all these techniques lack one or more elements necessary for their practical use in a clinical setting. Thus, confocal microscopy, although providing a superior spatial resolution, suffers from extremely limited field of view and complexity of implementing multi-wavelength imaging. In addition, this technique is very sensitive to small changes in the position of the investigated object. White-light polarization imaging, being simple and inexpensive, at the same time is unable to use spectral information and as a result does not provide necessary contrast. PpIX-fluorescence imaging is not specific enough; whereas the autofluorescence imaging tends to exaggerate tumor dimensions and is not capable of localizing the morpheaform BCC.

In view of the above-described deficiencies, a simpler, more time-efficient method would be desirable for mapping tumor borders. As such, in an embodiment of the present invention, there exists an apparatus for imaging a tissue region. The apparatus includes a polarized light emitter operable to emit light having a wavelength and a first polarization to the tissue region, a light detector operable to detect light remitted from the tissue region having the first polarization and light remitted from the tissue region having a second polarization perpendicular to the first polarization, and an analyzer operable to form an image from an intensity difference between detected light having the first polarization and detected light having the second polarization, whereby the wavelength corresponds to a depth of the image at or from the surface of the tissue region.

In another embodiment of the present invention, the predetermined wavelength of the polarized light is in a range of 200 nm and 2000 ml (i.e. ultraviolet ("UV")-visible ("VIS")-near infrared ("NIR")).

In yet another embodiment of the invention, the tissue region is stained with a contrast agent.

In yet another embodiment of the invention, the wavelength is varied to form a plurality of images at different depths.

In yet another embodiment of the invention, the analyzer creates a pseudo-3D image using respective images formed at different depths.

In yet another embodiment of the invention, there exists an imaging method for imaging a tissue region. The method includes the steps of emitting light having a wavelength and a first polarization to the tissue region, detecting light remitted from the tissue region having the first polarization and light remitted from the tissue region having a second polarization perpendicular to the first polarization, and forming an image from an intensity difference between the detected light having the first polarization and the detected light from the second polarization, whereby the wavelength corresponds to a depth of said image at or from the surface of the tissue region.

In yet another embodiment of the invention, there exists a recording medium having a program for controlling an imaging apparatus. The program may perform the steps of emitting light having a wavelength and a first polarization to the tissue region, detecting light remitted from the tissue region having a first polarization and light remitted from the tissue region having a second polarization perpendicular to said first polarization, and forming an image from an intensity difference between the detected light having said first polarization and the detected light from said second polarization, whereby said wavelength corresponds to a depth of said image at or from the surface of the tissue region.

DETAILED DESCRIPTION OF THE INVENTION

Figure 1:
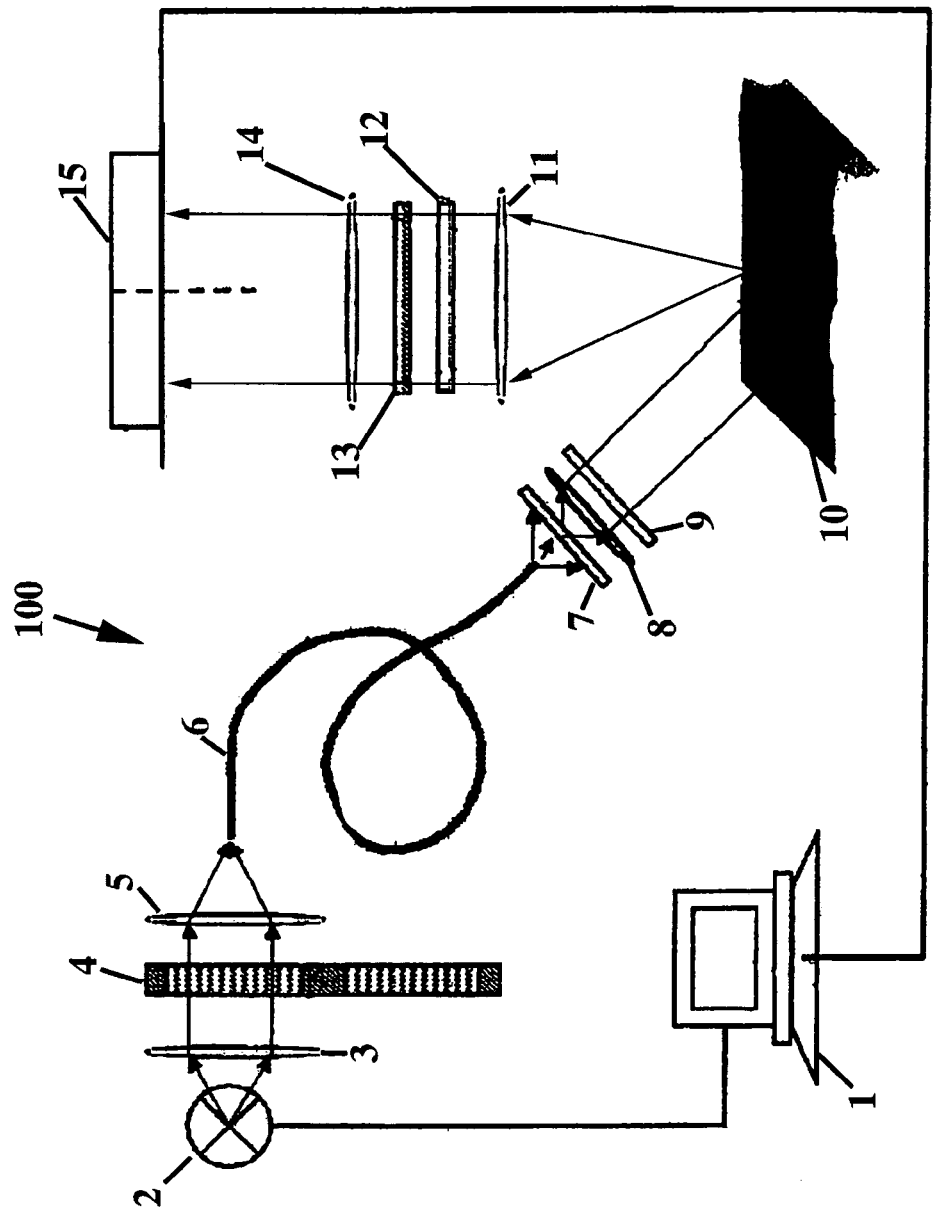
FIG. 1 depicts an example of an imaging apparatus in accordance with the present invention.

As shown in FIG. 1, a Computer 1 controls the imaging apparatus 100 to obtain images of organic tissue 10 such as non-melanoma skin cancers. Specifically, the computer 1 controls a lamp 2, such as a Xenon arc lamp, to emit light. The light passes through a lens 3 to a filter wheel 4. The filter wheel 4 may be provided with a number of interference filters to enable automatic wavelength selection and scanning. In a preferred embodiment, the interference filters will cover the spectral range from 390 nm to 750 nm. The monochromatic light produced by the filter wheel is coupled into a light guide 6, such as a liquid light guide, by a converging lens 5.

At the end of the light guide 6, the monochromatic light passes through a diffuser 7, such as a holographic diffuser, a collimator 8, such as a collimating achromatic lens, and a polarizer 9, such as a linearly polarizing filter. By passing the monochromatic light through the diffuser 7, collimator 8, and polarizer 9, homogeneous polarized light illumination of the tissue 10 can be achieved. The polarized light remitted from the tissue 10 passes through a lens 11, a filter 12, a polarizer 13, and a lens 14 is focused incident on to a the charge coupled device (CCD) camera 15. The filter 12 and/or polarizer 13 may be appropriately selected to allow for the study reflectance and/or polarization of the tissue images.

Figure 2:
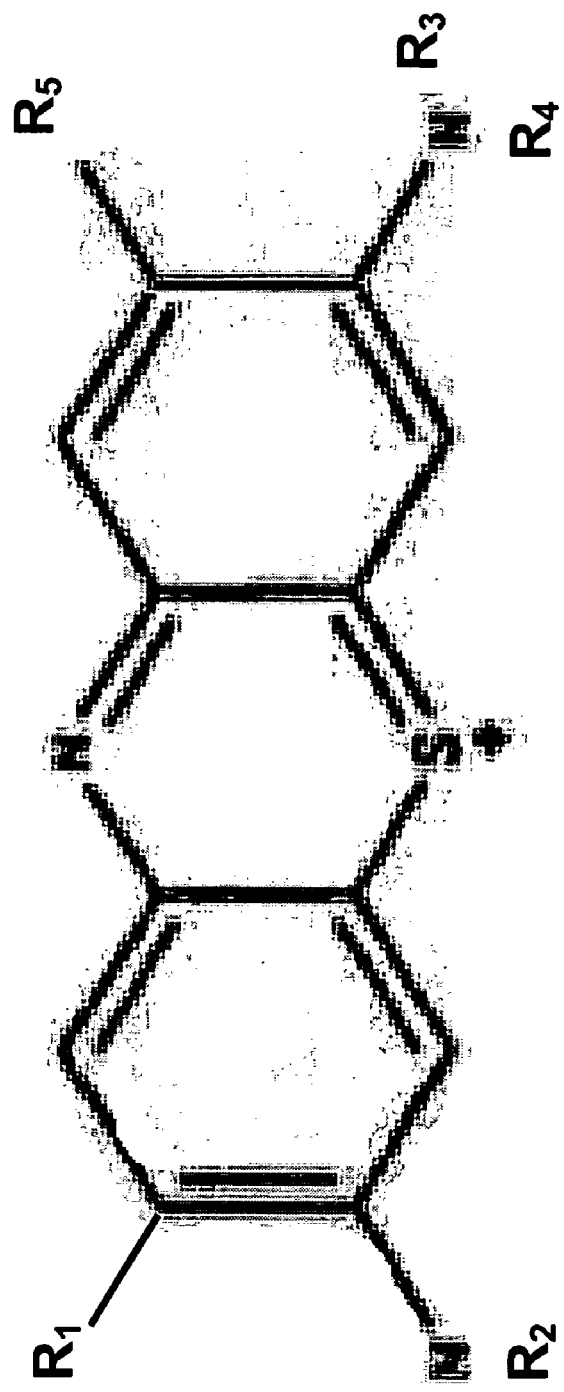
FIG. 2 depicts the chemical structure of Methylene Blue (MB) and Toluidine Blue (TB).
Figure 3:
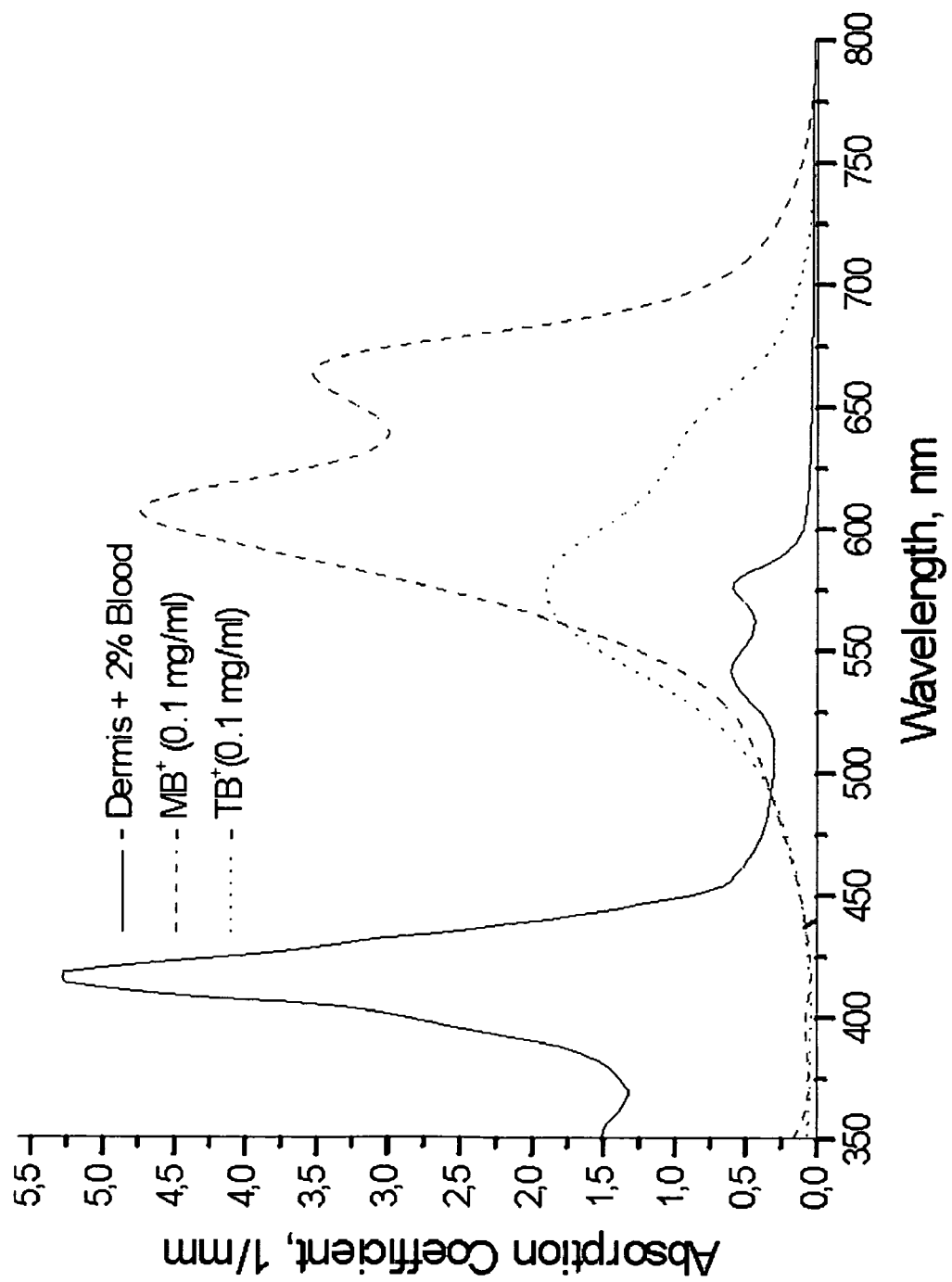
FIG. 3 depicts the absorption spectra of dermis stained with MB and/or TB.

In order to increase the contrast, the tissue 10 a contrast agent such as Methylene Blue (MB) and/or Toluidine Blue (TB) may be topically applied. FIG. 2 depicts the chemical structure of MB and TB. MB and/or TB are used to stain the tissue 10 in order to increase the contrast in the tissue images. FIG. 3 shows a light absorption spectra of dermis stained with MB and/or TB. The contrast agents exhibit a strong absorption of light having a wavelength that is in the 550 nm-700 nm region. In contrast, absorption in skin, which is dominated by two main chromophores, melanin and hemoglobin, exhibits a maximum with light having a wavelength around 400 nm. Therefore, spectrally resolved imaging using light having a wavelength in the range from 400 nm to 700 nm can delineate the areas of enhanced blood absorption and the areas of enhanced contrast agent absorption. Although MB and TB would be preferable, many other contrast agents may be used to stain the tissue in order to increase the contrast of the images.

Images of the tissue 10 are acquired using polarized light imaging (PLI). In the PLI process, polarized light is used to illuminate the tissue. Light remitted from the tissue 10 may include light that is polarized in a direction parallel to and perpendicular to the polarization of the incident light. The CCD camera 15 detects the remitted light and converts it into data for a first image ($I_\parallel$) and a second image ($I_\perp$). The first image is representative of the remitted light in a direction parallel to the incident light. The second image is representative of the remitted light in a direction perpendicular to the incident light. The first and second images are transmitted to computer 1 or the like to produce a difference image. The difference image ($I_A = I_\parallel - I_\perp$) is created by subtracting data for respective pixels between the first image and the second image.

Figure 4:
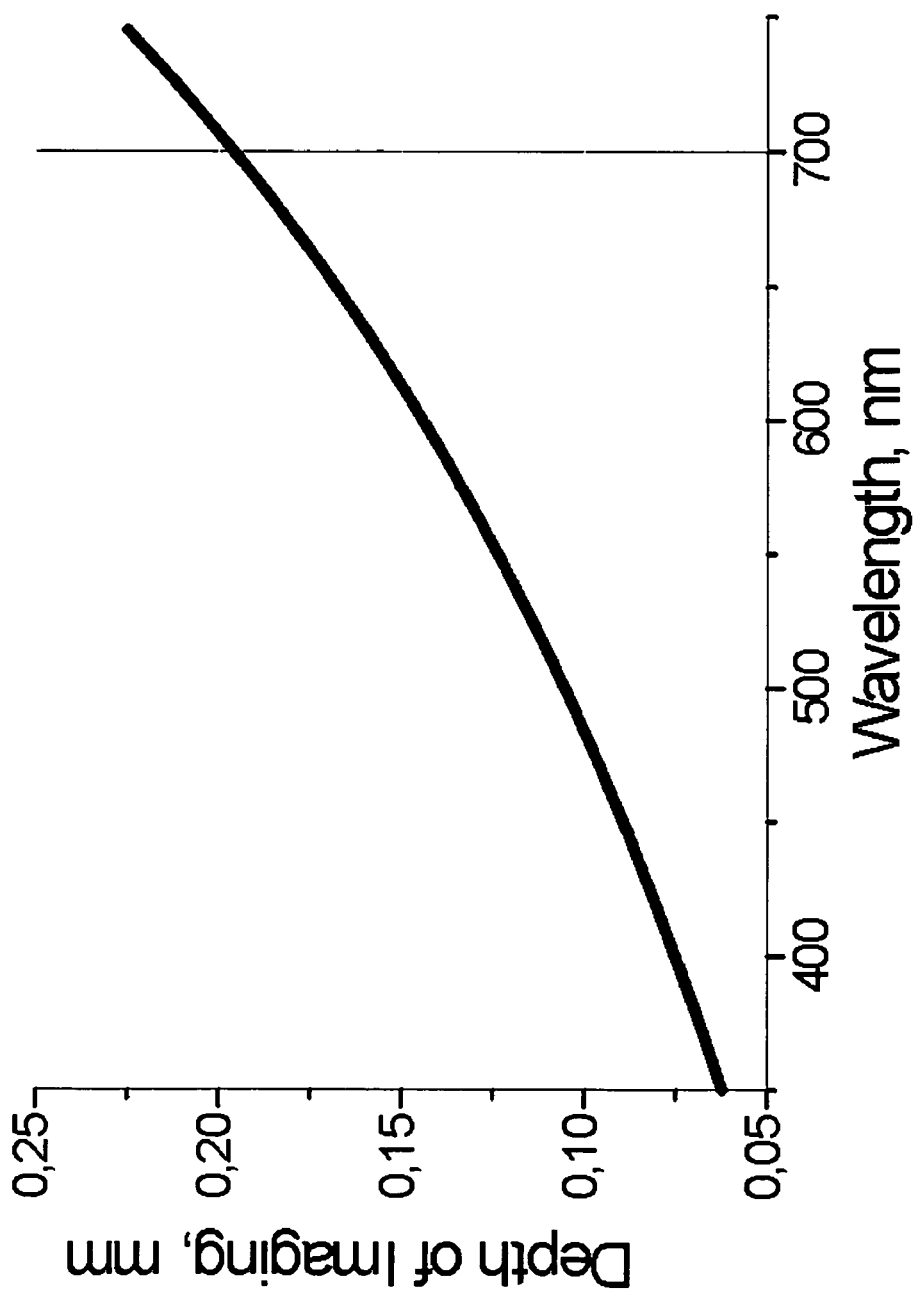
FIG. 4 depicts the dependence of the imaging depth (superficial image section thickness) on the wavelength of imaging light estimated using the known optical properties of skin.
Figure 5:
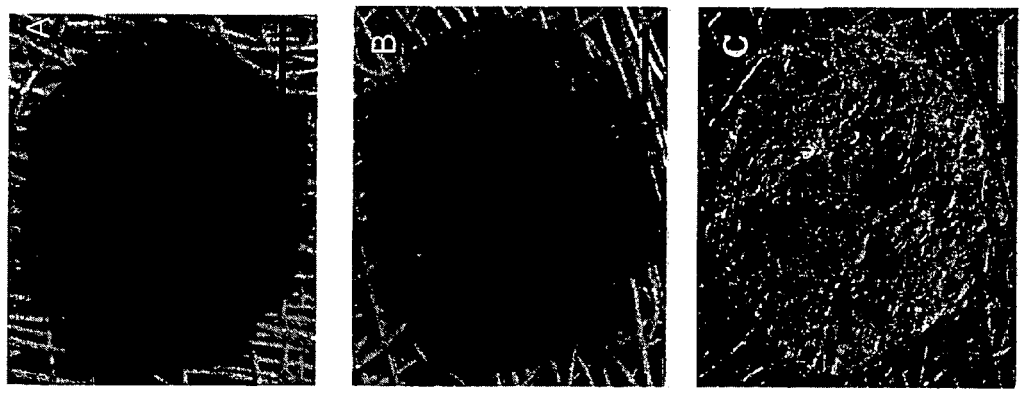
FIG. 5a-5c depicts images of skin with infiltrative BCC (site: lip) acquired at the wavelength $\lambda=410$ nm, scale bar=5 mm.
Figure 6:
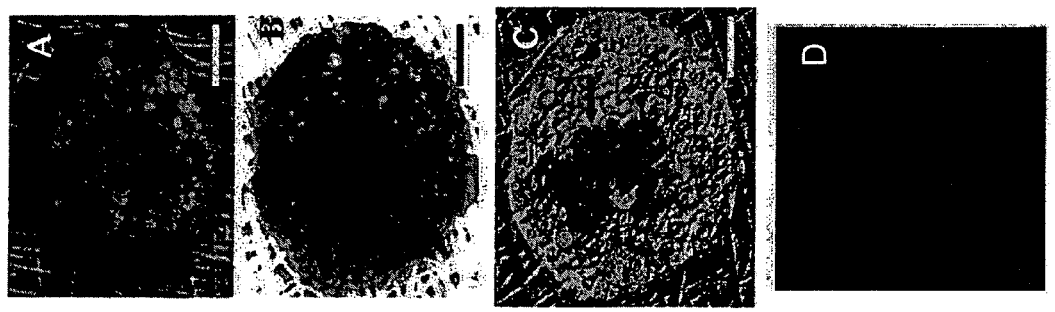
FIG. 6a-6d depicts images of skin with infiltrative BCC (site: lip), acquired at the wavelength $\lambda=610$ nm, scale bar: 5 mm.
Figure 7:
FIG. 7a-7e depicts images of skin with nodular and micronodular BCC (site: nose) acquired at the wavelength $\lambda=620$ nm, scale bar: 1 mm.
Figure 8:
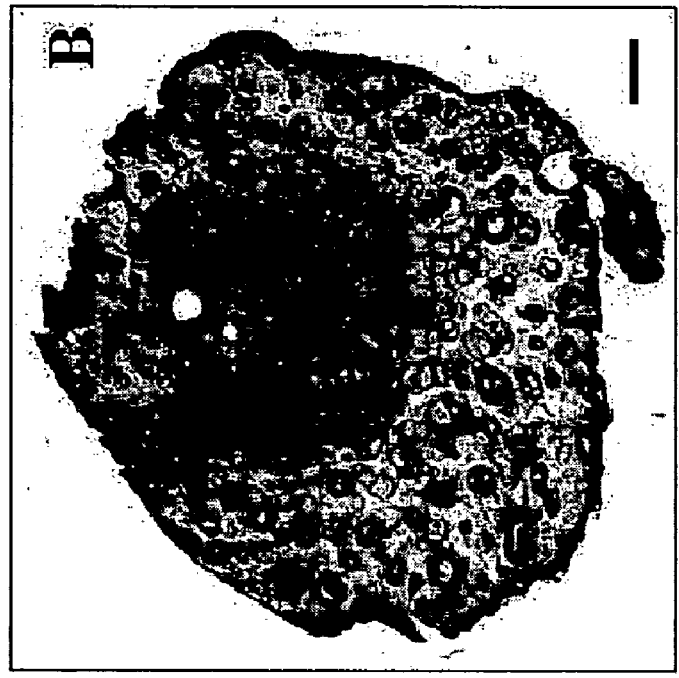
FIG. 8a-8b depicts an infiltrative BCC (site: chin).
Figure 8:
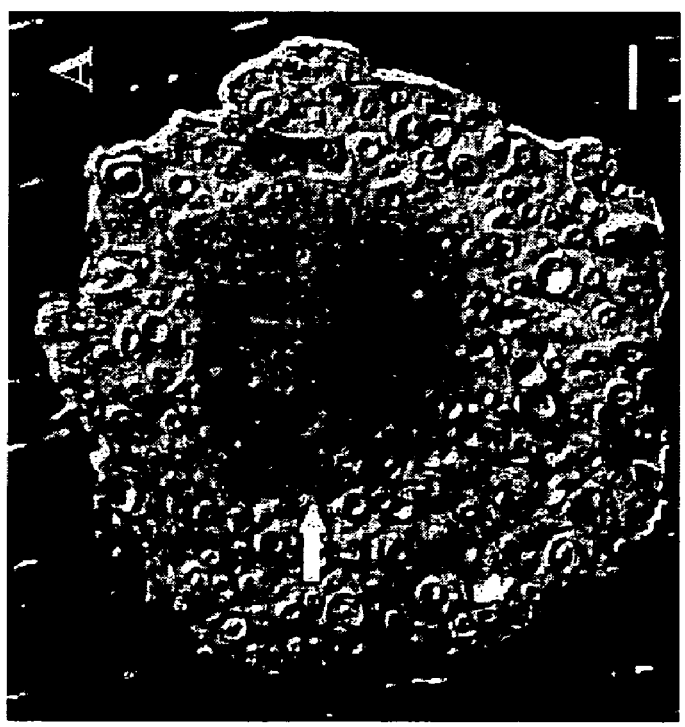
Figure 9:
FIG. 9a-9b depicts a nodular BCC (site: cheek).
Figure 9:
Figure 10:
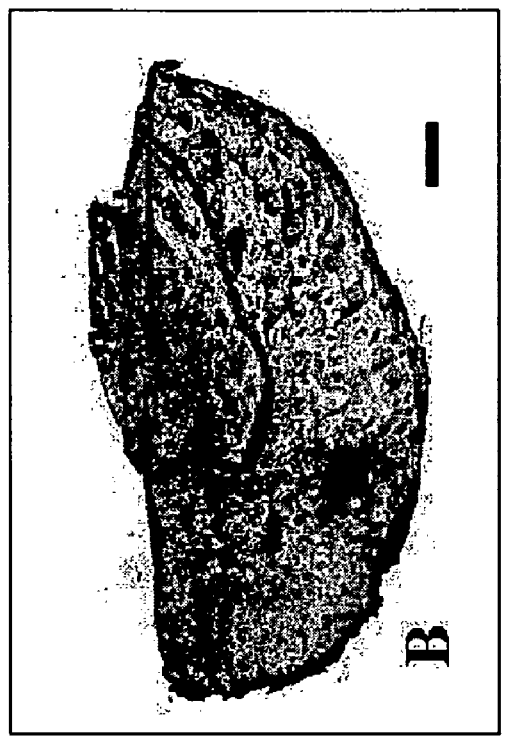
FIG. 10a-10b depicts a moderately differentiated SCC (site: ear).
Figure 10:

Using known optical properties of skin, FIG. 4 shows an estimated relationship between imaging depth in skin (superficial image section thickness) and the wavelength of imaging light. Single scattering does not change polarization of the elastically scattered light, while polarization of the multiply scattered light is randomized. Therefore when skin is illuminated with linearly polarized light, and two images are acquired using the remitted light polarized in the directions parallel ($I_\parallel$) and perpendicular ($I_\perp$) to the polarization of incident light, the difference image ($I_A = I_\parallel - I_\perp$) is produced mainly by single scattered light. Thus, the depth in the skin where the first back scattering event occurs is an adequate approximation for the thickness of the tissue layer, which contributes dominantly to the measured signal (imaging depth). This imaging depth, D, may be estimated if the scattering coefficient and the anisotropy factor of the tissue is known: $D=1/(\mu_s(1-g))$.

Using the optical properties of skin (Svaasand L O, Norvang L T, Fiskerstrand E J, Stopps E K S, Berns M W, Nelson J S: Tissue parameters determining visual appearance of normal skin and port-wine stains. *Las Med Sciences* 10: 55-65, 1995; Douven L F A, Lucassen G W: Retrieval of optical properties of skin from measurement and modeling the diffuse reflectance. *Proc SPIE* 3914: 312-323, 2000), it is possible to estimate the dependence of the section thickness of the skin images on the illumination wavelength. As shown in FIG. 4, at 400 nm, skin section thickness is approximately 75 µm, at 500 nm~100 µm, and at 700 nm~200 µm. By subtracting difference images acquired at different wavelengths, it is possible to obtain the images of thin skin layers below the surface of the tissue 10. For instance, if a first difference image is taken at a wavelength of 400 nm ($I_A^{400}$) and a second difference image is taken at a wavelength of 500 nm ($I_A^{500}$), if the second difference image is subtracted from the first difference image, the image of a thin layer at 75 µm from the surface can be obtained. Stacking such "layered" images may be used to build pseudo-3D images of the investigated tissue 10 by the computer 1.

The imaging apparatus employs a computer program to perform PLI. The computer program may be stored on a recording medium such as, but not limited to, a tape medium, a disk recording medium, a flash memory, etc.

EXAMPLES

The present invention will be further described by referring to FIGS. 5-10, which depict images of tissues acquired by the PLI method. As will be readily apparent, applying contrast agents, such as MB and TB, greatly improves the contrast of the tumor within the image.

Example images of infiltrative morpheaform BCC obtained at the wavelengths of 410 nm and 610 nm before and after staining are presented in FIGS. 5a-5c and 6a-6d. The images acquired at the wavelength of 410 nm before and after contrast agent application are presented in FIGS. 5a and 5b, respectively. In FIGS. 5a and 5b, the areas contaminated with blood appear dark in the image. On the upper right and lower left boundaries of the sample, the Mohs stain can be seen. Due to high blood content in the sample and enhanced hemoglobin absorption at 410 nm, it is difficult to locate the tumor in the conventional images, presented in FIGS. 5a and b. FIG. 5a (specimen before staining) does not differ significantly from FIG. 5b (specimen after staining) because, unlike blood, TB does not absorb light in the blue spectral range. Some blood was partially removed from the skin during staining and rinsing procedures, accounting for the differences in the adherent blood patterns in the images in FIGS. 5a and 5b. The superficial image, $I_A^{410}$, at 410 nm is shown in FIG. 5c. The section thickness of the superficial image obtained at 410 nm is approximately 75 µm (see FIG. 4). The absence of dark areas in the image $I_A^{410}$ suggests that there is no hemoglobin within the most superficial 75 µm of the tissue. Superficial hemoglobin was removed from the skin during staining and rinsing.

In FIGS. 6a, b the conventional images of the same infiltrative BCC tumor acquired before (FIG. 6a) and after (FIG. 6b) TB staining at the wavelength of 610 nm. This wavelength corresponds to the absorption band of TB (see FIG. 3). FIG. 6c presents superficial image, $U_A^{610}$, of the tumor acquired at the same wavelength of 610 nm. In contrast, to FIG. 5a in FIG. 6a no blood is noticeable, since at 610 nm hemoglobin absorption is weak. Comparison of FIGS. 6a (image of unstained tissue) and 6b (image of the stained tissue) confirms that the contrast agent stains the tumor to a much greater extent than healthy tissue and shows that topical application of TB significantly enhances contrast of the tumor in the image. Section thickness of the superficial image at 610 nm is approximately 150 µm, which is much thicker than Mohs frozen section (5 µm). Nonetheless, dark area in the image clearly delineates lesion boundaries, which correlate well with the margins outlined by the surgeon in the image of histological slide of the same tumor (FIG. 6d). It should be noted that the tumor could be identified in each of the superficial images presented (i.e. $I_A^{410}$ (FIG. 5c) and $I_A^{610}$ (FIG. 6c)). In the images $I_A^{410}$, acquired at 410 nm, the tumor appears as a structureless, homogeneous area while in the image $I_A^{610}$ the contrast of the tumor comparatively to normal skin is enhanced by the increased absorption of the contrast agent that is retained in the tumor.

Example images of the nodular and micronodular BCC acquired at the wavelength of 620 nm are shown in FIGS. 7a and 7b. Conventional and superficial images of unstained tissue are presented in FIGS. 7a and 7b, respectively. Tumor margins are hardly visible in the conventional image, while in the superficial image the tumor boundaries could be delineated even without staining. Conventional and superficial ($I_A^{620}$) images of the same specimen stained with TB are shown in FIGS. 7c and 7d. In both images the tumor is very dark and is easily identified. Comparison of the images in FIGS. 7b, 7c, and 7d with frozen H&E presented in FIG. 7e confirms that in general the location and the shape of the tumor were identified correctly in all the images. At the same time, the superficial image acquired before staining and the conventional image of the stained specimen make the tumorous tissue appear as a single tumor nest, whereas the superficial image of stained tissue reveals three closely seated tumor lobules. The reasons for these discrepancies are the following. The image in FIG. 7b is formed by the light that is remitted from all the depth of the tumor sample ($\geq 1$ mm thick). Therefore the conventional image of stained tissue (FIG. 7b) provides a superior contrast, but does not allow any depth resolution, which makes the detailed comparison with 5 μm thick H&E section (FIG. 7e) impossible. In contrast, the superficial imaging of the unstained tumor probes the layer of 150 μm, but obviously does not provide sufficient contrast to distinguish fine details of the imaged specimen. The combination of tissue staining and polarized light superficial imaging provides both strong contrast of the tumor in the image and depth resolution of approximately 150 μm. Detailed comparison of the images in FIG. 7d with frozen H&E presented in FIG. 7e confirms that the number and location of the tumor lobules were identified correctly in the image $I_A^{620}$ and proves that PLI enables imaging of the superficial tissue layer alone.

FIGS. 8a and 8b depict a comparison of (a) the superficial image, $I_A^{600}$, acquired at $\lambda=600$ nm (section thickness ~150 μm, stain: TB) with a (b) histological frozen section prepared during Mohs surgery (section thickness ~5 μm, stain: H&E) for infiltrative BCC (site: chin) at a scale bar of 1 mm. FIGS. 9a and 9b depict a comparison of (a) the superficial image, $I_A^{620}$, ($\lambda=620$ nm, section thickness ~150 μm, stain: MB) and (b) histological frozen section prepared during Mohs surgery (section thickness ~5 μm, stain: H&E) for nodular BCC (site: cheek) at a scale bar of 1 mm. FIGS. 10a and 10b depict a comparison of (a) the superficial image, $I_A^{620}$, ($\lambda=620$ nm, section thickness ~150 μm, stain: TB) and (b) histological frozen section prepared during Mohs surgery (section thickness ~5 μm, stain: H&E) for moderately-differentiated SCC (site: ear) at a scale bar of 1 mm.

MODIFICATIONS

Although preferred embodiments of the present invention and modifications thereof have been described in detail herein, it is to be understood that this invention is not limited to these embodiments and modifications, and that other modifications and variations may be effected by one skilled in the art without departing from the spirit and scope of the invention as defined by the appended claims.

For instance, the imaging apparatus is not limited to the embodiment shown in FIG. 1. Such apparatus may be included in a single unit or such apparatus may be included in an endoscope.

Further, although the present invention makes use of MB and TB to stain the tissue, many other contrast agents can be used to stain the tissue thereby increasing the contrast of the tumor in the images.

For instance, chromophores and photosensitizers may be used to enhance imaging contrast. As used herein, a "chromophore" means any light-absorbing chemical compound that is useful for enhancing image contrast by the methods and apparatus described. Chromophores include photosensitizers, drugs, dyes, microparticles, nanoparticles, or stains which absorb light. As used herein, "photosensitizer" means a chemical compound that produces a biological effect upon photoactivation or a biological precursor of a compound that produces a biological effect upon photoactivation. For the purpose of this invention, it is not necessary that a photosensitizer be used. However, many photosensitizers have been developed specifically for their ability to localize within cancerous tumors. Photosensitizers also must absorb light, in order to function as a photosensitizer (i.e. to be activated by light). Therefore, photosensitizers are a useful part of the large number of light-absorbing dyes and drugs, which can be used to enhance image contrast in the present invention.

Porphyrins and synthetic, modified porphyrins have traditionally been used as photosensitizers for photodynamic therapy (PDT). Porphyrins are the backbones of the molecule heme, the chief constituent of hemoglobin, which is the carrier of oxygen in red blood cells. Porphyrins, in an oxygen-rich environment, can absorb energy from photons and transfer this energy to surrounding oxygen molecules. At a specific wavelength corresponding with that of incident light, porphyrin is excited to the singlet excited state ($^1P^*$). This singlet excited porphyrin molecule can decay back to the ground state ($P^0$) with release of energy in the form of fluorescence. If the lifetime of the singlet state is long enough, it is possible for the singlet state to be converted to a triplet excited state ($^3P^*$), which can transfer energy to another triplet state. A molecule that is present in great abundance in cells is oxygen, which naturally occurs in $O_2$ form. This dioxygen molecule has a triplet ground state, and provided that the energy of the $^3P^*$ molecule is higher than that of its product, dioxygen in its triplet state is converted into the highly toxic singlet oxygen.

As stated above, singlet oxygen, as well as free radicals that are also produced during the photoactivation process, is extremely reactive and can damage proteins, lipids, nucleic acids, and other cellular components. Cellular responses to singlet oxygen are complex, but in general, singlet oxygen causes phospholipid peroxidation leading to cell membrane damage and vessel occlusion-mediated ischemia, causing necrosis or apoptosis in the cell of interest. This mechanism of killing differs from cellular damage induced by radiation treatment, where γ-radiation is used to generate DNA double strand breaks which if unresolved, will ultimately result in cell death.

Photosensitizers known in the art are selected for therapeutic uses according to: 1) efficacy in delivery, 2) proper localization in target tissues, 3) wavelengths of absorbance, 4) proper excitatory wavelength, and 5) purity, pharmacokinetics, metabolism, and reduced toxicity. Photosensitizers for clinical use are optimally amphiphilic, meaning that it must share the opposing properties of being water-soluble, yet hydrophobic. This is not an absolute requirement for the present invention, but is a preferable characteristic.

When delivered intravenously, a photosensitizer should be water-soluble in order to pass through the bloodstream systemically, however it should also be hydrophobic enough to pass across cell membranes. Modifications, such as attaching polar residues (amino acids, sugars, and nucleosides) to the hydrophobic porphyrin ring, can alter polarity and partition coefficients to desired levels. Similarly, when applied topically (directly) to the tissue prior to imaging in this invention, photosensitizers used as a contrast-enhancing agent may preferentially partition to, adhere to, and/or bind to cancerous tumors or the surrounding normal tissues. In this invention, absorption by the photosensitizer or other light-absorbing dye or drug, is used to enhance image contrast for detection of the tumor.

Photosensitizers of the present invention can bind to lipoproteins that are present in the bloodstream and are transported primarily to cells undergoing rapid division, such as tumors. Rapidly dividing cells require a greater amount of lipoproteins, and as a result, photosensitizers are selectively delivered to these cells at a higher level and with faster kinetics.

Preferably, chromophores of the present invention absorb light at one or more wavelength bands in the spectral region between 200 nm and 2000 nm, i.e., the optical part of the electromagnetic spectrum. It is not necessary that the chromophore absorb light at long wavelengths in this spectrum, i.e. at wavelengths which tend to penetrate deeply into tissue compared with short wavelengths. Chromophores and photosensitizers of the invention can be any known in the art, including, but not limited to, the following:

Tissue Dyes and Stains

A large number of stains and dyes are used in pathology for staining tissue samples prior to imaging with a conventional microscope. Some stains are non-toxic and preferentially bind to cancerous tumors in vivo. These chromophores are called vital stains, and are of particular interest and utility for this invention. In particular, dyes or stains with a delocalized cationic charge are capable of selective binding and retention in tumors. These include rhodamines such as rhodamine 123, phenothiazinium dyes methylene blue, and toluidine blue. Other vital stains such as rose bengal and eosin, which are red-pink stains binding to collagen in vivo, can be used.

Porphyrins and Hydroporphyrins

Photofrin® RTM (porfimer sodium), hematoporphyrin IX, hematoporphyrin esters, dihematoporphyrin ester, synthetic diporphyrins, O-substituted tetraphenyl porphyrins (picket fence porphyrins), 3,1-meso tetrakis (o-propionamido phenyl) porphyrin, hydroporphyrins, benzoporphyrin derivatives, benzoporphyrin monoacid derivatives (BPD-MA), monoacid ring "a" derivatives, tetracyanoethylene adducts of benzoporphyrin, dimethyl acetylenedicarboxylate adducts of benzoporphyrin, endogenous metabolic precursors, δ-aminolevulinic acid, benzonaphthoporphyrazines, naturally occurring porphyrins, ALA-induced protoporphyrin IX, synthetic dichlorins, bacteriochlorins of the tetra(hydroxyphenyl) porphyrin series, purpurins, tin and zinc derivatives of octaethylpurpurin, etiopurpurin, tin-etio-purpurin, porphycenes, chlorins, chlorin $e_6$, mono-1-aspartyl derivative of chlorin $e_6$, di-1-aspartyl derivative of chlorin $e_6$, tin(IV) chlorin $e_6$, meta-tetrahydroxyphenylchlorin, chlorin $e_6$ monoethylendiamine monamide, verdins such as, but not limited to zinc methyl pyroverdin (ZNMPV), copro II verdin trimethyl ester (CVTME) and deuteroverdin methyl ester (DVME), pheophorbide derivatives, and pyropheophorbide compounds, texaphyrins with or without substituted lanthanides or metals, lutetium (III) texaphyrin, gadolinium(III) texaphyrin.

Porphyrins, hydroporphyrins, benzoporphyrins, and derivatives are all related in structure to hematoporphyrin, a molecule that is a biosynthetic precursor of heme, which is the primary constituent of hemoglobin, found in erythrocytes. Chlorins and bacteriochlorins are also porphyrin derivatives, however these have the unique property of hydrogenated exo-pyrrole double bonds on the porphyrin ring backbone, allowing for absorption at wavelengths greater than 650 nm. Chlorins are derived from chlorophyll, and modified chlorins such as meta-tetra hydroxyphenylchlorin (mTHPC) have functional groups to increase solubility. Bacteriochlorins are derived from photosynthetic bacteria and are further red-shifted to ~740 nm.

Purpurins, porphycenes, and verdins are also porphyrin derivatives. Purpurins contain the basic porphyrin macrocycle, but are red-shifted to ~715 nm. Porphycenes have similar absorption wavelengths as hematoporphyrin (~635 nm), and are synthetic stable compounds with avidity for cancerous tumors. Verdins contain a cyclohexanone ring fused to one of the pyrroles of the porphyrin ring. Phorbides and pheophorbides are derived from chlorophylls and have been used as PDT drugs; these also can be used as chromophores in this invention. Texaphyrins are new metal-coordinating expanded porphyrins. The unique feature of texaphyrins is the presence of five, instead of four, coordinating nitrogens within the pyrrole rings. This allows for coordination of larger metal cations, such as trivalent lanthanides. Gadolinium and lutetium are used as the coordinating metals.

Cyanine and Other Photoactive Dyes

Merocyanines, phthalocyanines with or without metal substituents, chloroaluminum phthalocyanine with or without varying substituents, sulfonated aluminum PC, ring-substituted cationic PC, sulfonated AlPc, disulfonated and tetrasulfonated derivative, sulfonated aluminum naphthalocyanines, naphthalocyanines with or without metal substituents and with or without varying substituents, tetracyanoethylene adducts, nile blue, crystal violet, azure β chloride, rose bengal, benzophenothiazinium compounds, phenothiazine derivatives including methylene blue.

Cyanines are deep blue or purple compounds that are similar in structure to porphyrins. However, these dyes are much more stable to heat, light, and strong acids and bases than porphyrin molecules. Cyanines, phthalocyanines, and naphthalocyanines are chemically pure compounds that absorb light of longer wavelengths than hematoporphyrin derivatives with absorption maximum at about 680 nm. Phthalocyanines, belonging to a new generation of substances for PDT are chelated with a variety of metals, chiefly aluminum and zinc, while these diamagnetic metals enhance their phototoxicity. A ring substitution of the phthalocyanines with sulfonated groups will increase solubility and affect the cellular uptake. Less sulfonated compounds, which are more lipophilic, show the best membrane-penetrating properties and highest biological activity. The kinetics are much more rapid than those of HPD, with high tumor to tissue ratios (8:1) reached after 1-3 hours. The cyanines are eliminated rapidly and almost no drug remains in the tumor after 24 hours.

Other photoactive dyes such as methylene blue and rose bengal, are also used for PDT. Methylene blue is a phenothiazine cationic dye that is exemplified by its ability to specifically target mitochondrial membrane potential. Specific tumoricidal effects in response to cationic phenothiazine dyes are thought to be due to the electrical potential across mitochondrial membranes in tumor cells. Compared to normal cells, the potential in tumor cells is much steeper, leading to a high accumulation of compounds with delocalized positive charges (i.e. cationic photosensitizers). Rose-bengal and fluorescein are xanthene dyes that can be used in PDT, and as chromophores in this invention. Rose bengal diacetate is an efficient, cell-permeant generator of singlet oxygen. It is an iodinated xanthene derivative that has been chemically modified by the introduction of acetate groups. These modifications inactivate both its fluorescence and photosensitization properties, while increasing its ability to cross cell membranes. Once inside the cell, esterases remove the acetate groups and restore rose bengal to its native structure. This intracellular localization allows rose bengal diacetate to be a very effective photosensitizer.

Other Chromophores

Diels-Alder adducts, dimethyl acetylene dicarboxylate adducts, anthracenediones, anthrapyrazoles, aminoanthraquinone, phenoxazine dyes, chalcogenapyrylium dyes such as cationic selena and tellurapyrylium derivatives, cationic imminium salts, tetracyclines, and anionic dyes such as Evan's Blue, congo red, and trypan blue.

Immunoconjugates

The chromophore or photosensitizer can optionally be linked to a targeting moiety. In a preferred embodiment, the targeting moiety is an antibody. The antibody component can bind with specificity to an epitope present on the surface of a tumor cell. "Binding with specificity" means that non-cancer cells are either not specifically bound by the antibody or are only poorly recognized by the antibody. The antibodies can comprise whole native antibodies, bispecific antibodies; chimeric antibodies; Fab, Fab', single chain V region fragments (scFv) and fusion polypeptides. Preferably, the antibodies are monoclonal. In this embodiment, the carrier molecule, e.g. antibody, provided additional specificity for binding of the chromophore to tumor cells or other components of cancerous tumors.

Further, the contrast agent used to stain the tissue may, in addition to being applied topically, be given intravenously, subcutaneously or as a pill.

Further, although the above description is directed to the demarcation of nonmelanoma skin cancer, the present invention may be used for imaging any tissue surface. For instance, it may be used for detection and demarcation of the cancers of other organs or acquire images of the gastrointestinal tract or connective tissue. It may also be used for the demarcation of other skin conditions as well as imaging the mouth, pharynx, and larynx, tracheo-bronchial tree, esophagus, bladder, colon, vagina, cervix, etc.

The invention claimed is:

1. A method for obtaining images of skin condition in skin tissue, the method comprising the steps of:
    (a) applying a contrast agent to the skin tissue;
    (b) illuminating the skin tissue with polarized light of a first wavelength in an absorption range of the contrast agent and a second wavelength outside an absorption range of the contrast agent;
    (c) detecting remitted light that is polarized in a direction parallel to and perpendicular to a polarization of the polarized light;
    (d) for each wavelength, converting the remitted light into first data and second data, the first data being representative of the remitted light in a direction parallel to the polarized light and the second data being representative of the remitted light in a direction perpendicular to the polarized light;
    (e) producing a difference image for each wavelength by subtracting the respective second data from the first data;
    (f) subtracting the second wavelength difference image from the first wavelength difference image to create an image of a layer below a surface of the skin tissue in which background noise is largely cancelled out; and
    (g) mapping a skin condition border based on the image.

2. A method as recited in claim 1, further comprising the step of estimating a depth of the layer based upon $$D=1/(\mu_s(1-g))$$

where D is the depth, $\mu_s$ is a scattering factor of the skin tissue and g is a anisotropy factor of the skin tissue.

3. A method as recited in claim 1, further comprising the steps of:
    repeating steps (b)-(f) with a plurality of wavelengths to create additional images of layers at varying depths below the surface; and
    stacking the image and the additional images to create a pseudo-3D image.

4. A method as recited in claim 1, wherein the contrast agent is selected from the group consisting of Methylene Blue and Toluidine Blue, and the first wavelength is about 390 nm and the second wavelength is about 750 nm.

5. An apparatus for imaging a tissue region, comprising:
    a linear optical system including:
        (a) a polarized light emitter operable to emit light having at a plurality of user-selected wavelengths, the light having a first polarization direction with respect to the tissue region;
        (b) a light detector operable to detect light remitted from the tissue region having said first polarization direction and light remitted from the tissue region having a second polarization direction perpendicular to said first polarization direction; and
        (c) an analyzer operable to:
            i) form a first difference image for a first wavelength of the light by subtracting the respective detected light having the second polarization direction from the detected light having the first polarization direction;
            ii) form a second difference image for a second wavelength of the light by subtracting the respective detected light having the second polarization direction from the detected light having the first polarization direction;
            iii) create a third image of a layer in the tissue region by subtracting the second difference image from the first difference image; and
            (iv) map a cancer tumor border in the tissue region based on the third image.

6. The apparatus according to claim 5, whereby the wavelengths are in a range of 200 nm and 2000 nm.

7. The apparatus according to claim 5, whereby the wavelengths are in a range of 390 nm and 750 nm.

8. The apparatus according to claim 5, wherein the tissue region is skin and the third image is in a range of 1 μm to 3 mm from a surface of the skin tissue region and wherein the range is determined by a spectral range of the light employed and by optical properties of the skin tissue region.

9. The apparatus according to claim 8, wherein the analyzer creates a pseudo-3D image using a plurality of images formed at different depths.

10. An imaging method for imaging a tissue region comprising the steps of:
    emitting light having a first wavelength and a parallel polarization direction with respect to the tissue region;
    detecting parallel light remitted from the tissue region having the parallel polarization direction and perpendicular light remitted from the tissue region having a polarization direction perpendicular to the parallel polarization direction;
    forming a difference image by subtracting the perpendicular light from the parallel light, whereby a depth of the difference image at or from the surface of the tissue region is determined in accordance with $$D=1/(\mu_s(1-g))$$

where D is the depth, $\mu_s$ is a scattering factor of the tissue region and g is an anisotropy factor of the tissue region such that as the wavelength becomes larger, the depth becomes larger;

emitting light having a second wavelength and a parallel polarization direction with respect to the tissue region;

detecting parallel light remitted having the parallel polarization direction and perpendicular light remitted from the tissue region having a polarization direction perpendicular to the parallel polarization direction as a result of the second wavelength illuminating the tissue region;

forming a second difference image related to the second wavelength by subtracting the respective perpendicular light from the respective parallel light; and creating an image using a plurality of the difference images.

11. The imaging method of claim 10, further comprising the step of applying a contrast agent to the tissue region.

12. The imaging method of claim 10, wherein each of the difference images is in a range of 1 µm to 3 mm from a surface of the tissue region, and wherein said range is determined by a spectral range of the light employed and the optical properties of the tissue region.

13. The imaging method of claim 12, further comprising the step of creating a pseudo-3D image using a plurality of images formed at different depths.

14. An imaging apparatus comprising:
means for illuminating organic tissue with polarized light of a first wavelength and a second wavelength;
means for detecting remitted light that is polarized in a direction parallel to and perpendicular to a polarization of the polarized light;
means for converting the remitted light into first data and second data for each wavelength, the first data being representative of the remitted light in a direction parallel to the polarized light and the second data being representative of the remitted light in a direction perpendicular to the polarized light;
means for producing a difference image for each wavelength by subtracting the respective second data from the first data; and
means for subtracting the second wavelength difference image from the first wavelength difference image and creating an image of a layer below a surface of the organic tissue.

15. An imaging apparatus as recited in claim 14, wherein the means for illuminating is an arc lamp and a polarizer, the means for detecting and converting is a CCD camera, and the means for producing and subtracting is a processor.

16. An imaging method comprising the steps of:
obtaining a first image of a tissue using a predetermined wavelength having a first polarization direction;
obtaining a second image of the tissue using the predetermined wavelength and a second polarization direction perpendicular to the first polarization direction;
forming a first difference image from the first image and the second image;
obtaining a third image of the tissue using a second predetermined wavelength having a first polarization direction;
obtaining a fourth image of the tissue using the second predetermined wavelength and a second polarization direction perpendicular to the first polarization direction; and
forming a second difference image from the first image and the second image generated from the second predetermined wavelength;
subtracting the second difference image from the first difference image to remove deep tissue data; and
creating an image of a superficial layer in the tissue.

* * * * *

UNITED STATES PATENT AND TRADEMARK OFFICE
CERTIFICATE OF CORRECTION

PATENT NO. : 7,627,363 B2 Page 1 of 1
APPLICATION NO. : 10/803329
DATED : December 1, 2009
INVENTOR(S) : Yaroslavsky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 697 days.

Signed and Sealed this

Second Day of November, 2010

David J. Kappos
*Director of the United States Patent and Trademark Office*